United States Patent [19]

Kanne et al.

[11] Patent Number: 5,189,060
[45] Date of Patent: * Feb. 23, 1993

[54] IMIDATE INSECTICIDES

[75] Inventors: David B. Kanne, Corte Madera; Karl J. Fisher, Petaluma; Michael D. Broadhurst, Novato, all of Calif.

[73] Assignee: Imperial Chemical Industries PLC, London, United Kingdom

[*] Notice: The portion of the term of this patent subsequent to Feb. 19, 2008 has been disclaimed.

[21] Appl. No.: 621,157

[22] Filed: Nov. 30, 1990

Related U.S. Application Data

[63] Continuation-in-part of Ser. No. 579,131, Sep. 6, 1990, abandoned, which is a continuation of Ser. No. 352,328, May 16, 1989, abandoned, and a continuation-in-part of Ser. No. 343,552, Apr. 27, 1989, Pat. No. 5,045,566, which is a continuation-in-part of Ser. No. 263,605, Oct. 31, 1988, abandoned, and a continuation-in-part of Ser. No. 264,746, Oct. 31, 1988, abandoned, each each 264,746, is a continuation-in-part of Ser. No. 122,877, Nov. 17, 1987, abandoned.

[30] Foreign Application Priority Data

Nov. 13, 1988 [IR] Iran ............................................ 27998
Nov. 15, 1988 [EP] European Pat. Off. ......... 88310775.7

[51] Int. Cl.⁵ ..................... A61K 37/52; A61K 31/21; C07D 213/643
[52] U.S. Cl. .................................... 514/508; 514/351; 514/357; 514/466; 558/9; 546/290; 546/300; 549/366; 549/439; 549/491
[58] Field of Search ............................ 558/9; 549/328; 514/508, 471

[56] References Cited

U.S. PATENT DOCUMENTS

| | | | |
|---|---|---|---|
| 4,994,488 | 2/1991 | Broadhurst et al. | 558/9 |
| 5,045,566 | 9/1991 | Broadhurst et al. | 514/508 |
| 5,089,623 | 2/1992 | Fisher | 546/300 |

FOREIGN PATENT DOCUMENTS 2212495 7/1989 United Kingdom ............... 558/9

*Primary Examiner*—Floyd D. Higel
*Attorney, Agent, or Firm*—Joel G. Ackerman

[57] ABSTRACT

Novel insecticides have the formula

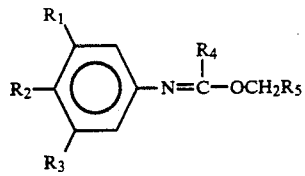

in which
$R_1$ is hydrogen, halogen, $C_1$-$C_4$ alkoxy, $C_1$-$C_4$ haloalkyl, $C_1$-$C_4$ haloalkoxy or $C_1$-$C_4$ haloalkylthio;
$R_2$ is hydrogen, halogen, $C_1$-$C_4$ alkyl, $C_1$-$C_4$ alkoxy, $C_1$-$C_4$ haloalkyl, $C_1$-$C_4$ haloalkoxy or $C_1$-$C_4$ haloalkylthio;
$R_3$ is hydrogen, halogen or $C_1$-$C_4$ haloalkyl; or
$R_1$ and $R_2$ taken together are $C_1$-$C_4$ alkylenedioxy or halo-$C_1$-$C_3$ alkylenedioxy; provided that $R_1$, $R_2$ and $R_3$ are not all hydrogen;
$R_4$ is methyl, ethyl, n-propyl, $C_3$-$C_7$ branched alkyl, $C_1$-$C_6$ haloalkyl, $C_2$-$C_4$ alkenyl; or cyclopropyl, optionally substituted by up to 4 methyl groups or up to 2 halogens;
$R_5$ is:

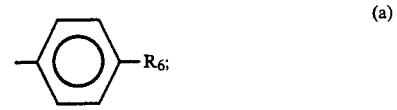

(a)

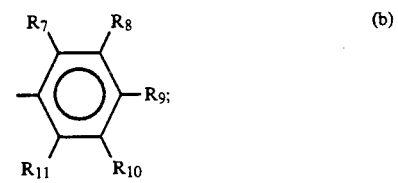

(b)

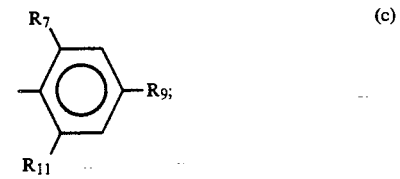

(c)

or

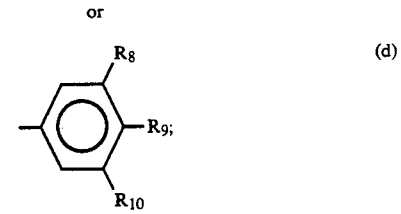

(d)

$R_6$ is phenyl, benzyl, $C_3$-$C_4$ alkenyl, or $C_3$ alkynyl;
$R_7$, $R_8$, $R_{10}$ and $R_{11}$ are each halogen; and
$R_9$ is methyl, methoxymethyl, methylthio, methylthiomethyl, hydroxymethyl, cyanomethyl, benzyl, $C_3$-$C_4$ alkenyl, $C_3$ alkynyl or propargylamino.

15 Claims, No Drawings

IMIDATE INSECTICIDES

CROSS-REFERENCE TO RELATED APPLICATIONS

This is a continuation-in-part of application Ser. No. 07/579,131, filed Sep. 6, 1990, now abandoned, which is a continuation of application Ser. No. 07/352,328, filed May 16, 1989, now abandoned. This is also a continuation-in-part of application Ser. No. 07/343,552, filed Apr. 27, 1989, now U.S. Pat. No. 5,045,566, which is a continuation-in-part of application Ser. Nos. 07/263,605 and 07/264,746, both filed Oct. 31, 1988, both abandoned, both of which are continuations-in-part of application Ser. No. 122,877, filed Nov. 17, 1987, now abandoned.

FIELD OF THE INVENTION

This invention relates to a series of novel insecticides having the general formula

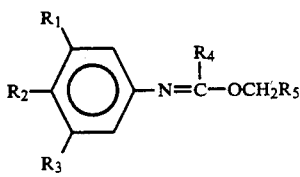

in which
$R_1$ is hydrogen, halogen, $C_1-C_4$ alkoxy, $C_1-C_4$ haloalkyl, $C_1-C_4$ haloalkoxy or $C_1-C_4$ haloalkylthio;
$R_2$ is hydrogen, halogen, $C_1-C_4$ alkyl, $C_1-C_4$ alkoxy, $C_1-C_4$ haloalkyl, $C_1-C_4$ haloalkoxy or $C_1-C_4$ haloalkylthio;
$R_3$ is hydrogen, halogen or $C_1-C_4$ haloalkyl; or
$R_1$ and $R_2$ taken together are $C_1-C_4$ alkylenedioxy or halo-$C_1-C_3$ alkylenedioxy;
provided that $R_1$, $R_2$ and $R_3$ are not all hydrogen;
$R_4$ is methyl, ethyl, n-propyl, $C_3-C_7$ branched alkyl, $C_1-C_6$ haloalkyl, $C_2-C_6$ alkenyl; or cyclopropyl, optionally substituted by up to 4 methyl groups or up to 2 halogens;
$R_5$ is:

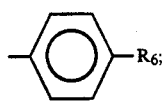 (a)

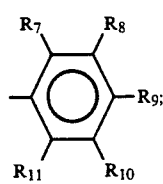 (b)

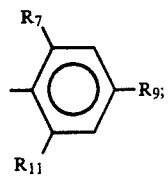 (c)

or

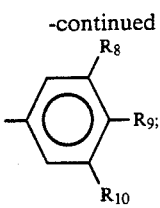 (d)

$R_6$ is phenyl, benzyl, $C_3-C_4$ alkenyl, or $C_3$ alkynyl;
$R_7$, $R_8$, $R_{10}$ and $R_{11}$ are each halogen; and
$R_9$ is methyl, methoxymethyl, methylthio, methylthiomethyl, hydroxymethyl, cyanomethyl, benzyl, $C_3-C_4$ alkenyl, $C_3$ alkynyl or propargylamino.

This invention also relates to insecticidal compositions comprising an insecticidally effective amount of a compound as defined above together with an insecticidally suitable diluent or carrier. In another aspect, this invention involves a method for controlling insects by administration of an insecticidally effective amount of a compound or composition of the invention to a locus where control is desired.

As used herein, the term "halogen" includes fluoro, chloro, bromo and iodo and is generally preferably fluoro or chloro. The term "alkylenedioxy" refers to a linking group -O-alkylene-O- in which the alkylene group (which may be straight or branched chain) has from 1 to 4 carbon atoms. Such groups include methylenedioxy (—O—CH$_2$—O'), 1,2-ethylenedioxy (—O—CH$_2$CH$_2$—O—), mono- or dihalomethylenedioxy (a methylenedioxy group in which one or both hydrogens is replaced by a halogen) and isopropylenedioxy [—O—C(CH$_3$)$_2$—O—]. The term "propargylamino" refers to the group —NHCH$_2$C≡CH. The terms "haloalkyl, haloalkoxy, haloalkylthio, or haloalkylenedioxy" include groups of such type substituted by one or more of the same or different halogens. For these halogen substituted groups, preferred halogens are fluoro, chloro and bromo, with fluoro being most preferred. Examples of such groups include difluoromethyl, trifluoromethyl, difluoromethoxy, trifluoromethoxy, difluorobromomethoxy, difluorochloromethoxy, difluoromethylenedioxy and halogenated analogs of the above containing more than one carbon atom.

The terms "alkyl", "alkoxy" and the like include both straight and branched chain groups having the indicated number of carbon atoms.

The term "alkenyl" includes both straight and branched chain mono-olefinic groups.

Preferred embodiments for $R_1$, $R_2$ and $R_3$ are hydrogen, halogen, ethoxy, difluoromethyl, trifluoromethyl, difluoromethoxy, trifluoromethoxy, 2,2,2-trifluoroethoxy and 1,1,2-trifluoro-2-chloroethoxy or for $R_1$ and $R_2$ taken together, methylenedioxy and difluoromethylenedioxy.

A preferred haloalkylthio group is trifluoromethylthio.

For group $R_4$, preferred substituents are ethyl, isopropyl, tertiary butyl, isopropenyl, dichloromethyl and cyclopropyl.

Preferred groups for substituent R5 include 2,3,5,6-tetrafluoro-4-propargylphenyl; 2,3,5,6-tetrafluoro-4-allyl-2,3,5,6-tetrafluoro-4-methoxymethylphenyl; 3,5-difluoro-4-propargylphenyl; 4-phenylphenyl; and 4-benzylphenyl.

PROCESSES FOR PREPARATION OF COMPOUNDS OF THIS INVENTION

Compounds of this invention may be prepared by one or both of two processes.

Process (A)

Many compounds of this invention may be prepared by reaction of an imidoyl halide (preferably chloride) with an alkali metal alkoxide according to the general reaction:

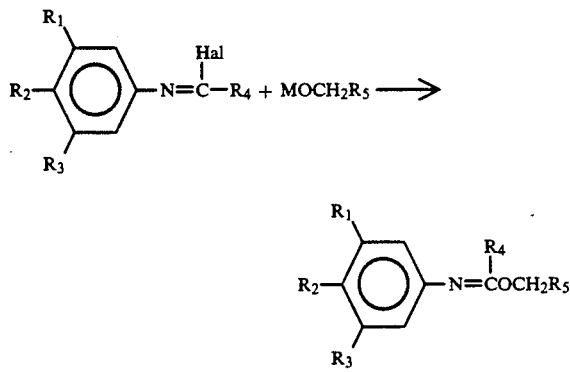

in which M is an alkali metal, preferably sodium or potassium, and Hal is halogen, particularly chloro or bromo.

This reaction is conducted at a temperature of from about −70° C. to about +65° C., most preferably at about room temperature, for a time which may range from about 5 minutes to about 24 hours. The reaction is conducted in the presence of a solvent, for example, an aromatic hydrocarbon such as benzene, toluene, or xylene or an ether, such as diethyl ether, diisopropyl ether, diisoamyl ether, dibutyl ether, furan, 1,2-dimethoxyethane, or tetrahydrofuran (preferably tetrahydrofuran). In some instances, apparent to those skilled in the art, it is advantageous to add the solution of the alkali metal alkoxide to a solution of the imidoyl halide or to use substantial excesses of alkoxide. The resulting product may be recovered by conventional techniques.

The alkoxide is produced by reaction of an appropriate alcohol, such as 2,3,5,6-tetrafluoro-4-methoxymethylbenzyl alcohol, with an alkali metal-containing base, for instance, an alkali metal hydride (e.g., potassium or preferably sodium hydride) in the presence of a solvent such as that used in reaction of the alkali metal alkoxide with the imidoyl halide. In general, this reaction is conducted at reflux temperature under an inert atmosphere for a time which may range up to about 2 hours.

The alcohols, if not commercially available, can be prepared according to known methods such as those described in the following references: U.S. Pat. Nos. 4,370,346 and 4,594,355; British Patent Applications 2,,122,616 and 2,207,917; European patent applications 196,156 and 271,240; and *J. Sci. Food & Agriculture* 18, 167 (1967).

The imidoyl halide may be prepared from the corresponding amine or amide. The amine is either generally available or may be prepared by procedures known in the art, for example, those described in " Compendium of Organic Synthetic Methods", Harrison et al. (Wiley-Interscience, New York, 1971).

The amide, if not available, may be produced by reaction of the amine with an acid halide

The temperature of this reaction ranges from about −40° C. to about +80° C. Suitable solvents include hydrocarbon solvents such as toluene and chlorinated hydrocarbon solvents such as methylene chloride, chloroform, carbon tetrachloride, ethylene dichloride, tetrachloroethane and the like, preferably methylene chloride. This reaction is conducted in the presence of a base, preferably a tertiary amine. Suitable bases include triethylamine, quinoline, dimethylaniline, diethylaniline, and pyridine. Triethylamine is the preferred base. The amide is recovered and purified by conventional means.

The imidoyl halide may be prepared from the amide by reacting it with a halogenating agent such as phosphorus pentachloride or phosgene in an organic solvent such as that utilized in the amide production (preferably methylene chloride) or alternatively using phosphorus oxychloride as the solvent. The reaction is carried out under an inert atmosphere for a time which may be up to 24 hours, preferably from 1 to 24 hours, at a temperature of from about 0° C. to about 110° C. Before the imidoyl chloride-containing product is passed to the final step, all substances, such as phosphorus oxychloride or hydrogen chloride, which can react with the alkoxide in the final step, should be removed. This can generally be accomplished by evaporation or distillation.

Process (B)

This process may be used as an alternative to process (A) for preparation of compounds of this invention from alcohols which are sensitive to, and could be adversely affected (e.g., decomposed) by, strong bases such as the alkali metal-containing bases (e.g., alkali metal hydrides) used to prepare the alkoxides. 2,3,5,6-tetrafluoropropargylbenzyl alcohol is an example of a base-sensitive alcohol.

Compounds of this type may be made by direct reaction of the alcohol with the imidoyl chloride in the presence of a tertiary amine base and a reaction-promoting amount of a 4-di(lower alkyl)aminopyridine, preferably 4-dimethylaminopyridine.

Tertiary amines which may be used in this process include trialkylamines such as trimethyl-, triethyl-, tri-n-butylamine and the like, including tertiary amines having mixed alkyl groups, N,N-dialkylanilines such as N,N-dimethylaniline, pyridine and various substituted pyridines.

Preferred tertiary amines, primarily for economical reasons, are triethylamine, N,N-dimethylaniline, and pyridine. The tertiary amine may even be an additional amount of the promoter 4-di(lower alkyl)aminopyridine, over and above that amount needed for promoting the reaction.

The tertiary amine is preferably used in a stoichiometric amount with respect to the alcohol, but may be used in excess of that amount. The promoter 4-di(lower alkyl)aminopyridine may be used in an amount from about 0.05 to about 1 equivalent per equivalent of alcohol, preferably from about 0.05 to about 0.15 equivalent per equivalent, most preferably about 0.1.

This process is preferably conducted at temperatures of from about 10° C. to about 50° C. Lower temperatures may be used, but the reaction rate would be much slower. The process is carried out in the presence of an inert solvent such as an aromatic hydrocarbon (for instance, benzene, toluene or xylene), a chlorinated solvent (such as methylene chloride, ethylene dichloride or chlorobenzene) or an ether (such as diethyl ether, dioxane or tetrahydrofuran).

While this process is particularly suitable for producing compounds from base-sensitive alcohols, it may also be used to produce compounds of this invention in general from other alcohols as described.

The following is an example of preparation of a compound of this invention.

Preparation of
N-(3-chloro-4-trifluoromethoxyphenyl)-0-(2,3,5,6-tetrafluoro-4-propargylbenzyl isobutyrylimidate In a flask, maintained at room temperature under a nitrogen atmosphere, were placed 500 milligrams (mg) (I.66 mmol) N-(3-chloro-4-trifluoromethoxyphenyl-)isobutyrimidoyl chloride, 0.16 grams (g) triethylamine, 50 mg 4-dimethylaminopyridine and 361 mg (1.66 mmol) 2,3,5,6-tetrafluoro-4-pro- pargylbenzyl alcohol. The mixture was stirred at room temperature for 72 hours, with the reaction monitored by gas chromatography. Then, 100 ml of hexane was added, the mixture filtered through silica and washed with 5% ethyl acetate/hexanes. The filtrates were combined and stripped of hexane with the temperature being kept below 30° C., to produce 380 mg of crude product, a low melting solid. The product was analyzed by gas chromatography and nuclear magnetic resonance spectroscopy and was determined to contain 62.5–66% of the desired product.

Representative compounds of this invention are illustrated by Tables I and II below.

TABLE I

| Compound No. | $R_1$ | $R_2$ | $R_3$ | $R_4$ | $R_6$ |
|---|---|---|---|---|---|
| 1 | Cl | $CF_3O$ | H | $i\text{-}C_3H_7$ |  |
| 2 | Cl | $CF_3O$ | H | $i\text{-}C_3H_7$ | $-CH_2-$⌬ |
| 3 | Cl | $CF_3O$ | H | $i\text{-}C_3H_7$ | $-CH_2CH=CH_2$ |
| 4 | Cl | $CF_3O$ | H | $i\text{-}C_3H_7$ | $-CH_2C(CH_3)=CH_2$ |
| 5 | Cl | $CF_3O$ | H | $i\text{-}C_3H_7$ | $-CH_2CH=CHCH_2$ |

TABLE II

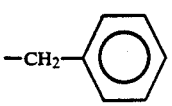

| Compound Number | $R_1$ | $R_2$ | $R_3$ | $R_4$ | $R_7$ | $R_8$ | $R_9$ | $R_{10}$ | $R_{11}$ |
|---|---|---|---|---|---|---|---|---|---|
| 6 | H | $CF_3$ | H | $i\text{-}C_3H_7$ | F | F | $-CH_2C\equiv CH$ | F | F |
| 7 | $-(OCH_2O)-$ | | H | $i\text{-}C_3H_7$ | F | F | $-CH_2OCH_3$ | F | F |
| 8 | $CF_3$ | H | H | $i\text{-}C_3H_7$ | F | F | $-CH_2OCH_3$ | F | F |
| 9 | $CF_3$ | H | H | $i\text{-}C_3H_7$ | F | F | $-C\equiv C-CH_3$ | F | F |
| 10 | Cl | F | H | $i\text{-}C_3H_7$ | F | F | $-CH_2OCH_3$ | F | F |
| 11 | Cl | F | H | $i\text{-}C_3H_7$ | F | F | $-CH_2C\equiv CH$ | F | F |
| 12 | H | $t\text{-}C_4H_9$ | H | $i\text{-}C_3H_7$ | F | F | $-CH_2OCH_3$ | F | F |
| 13 | $CF_3$ | H | H | $i\text{-}C_3H_7$ | F | F | $-CH_2C\equiv CH$ | F | F |
| 14 | $-(OCH_2O)-$ | | H | $i\text{-}C_3H_7$ | F | F | $-CH_2C\equiv CH$ | F | F |
| 15 | Cl | $CF_3O$ | H | $i\text{-}C_3H_7$ | F | F | $-CH_2C\equiv CH$ | F | F |
| 16 | F | $CF_3O$ | H | $i\text{-}C_3H_7$ | F | F | $-CH_2C\equiv CH$ | F | F |
| 17 | Cl | $CF_3O$ | H | $i\text{-}C_3H_7$ | F | F | $-CH_2CH=CH_2$ | F | F |
| 18 | $-(OCF_2O)-$ | | H | $i\text{-}C_3H_7$ | F | F | $-CH_2C\equiv CH$ | F | F |
| 19 | H | $CF_3O$ | H | $i\text{-}C_3H_7$ | F | F | $-CH_2C\equiv CH$ | F | F |
| 20 | Cl | H | H | $i\text{-}C_3H_7$ | F | F | $-CH_2C\equiv CH$ | F | F |
| 21 | F | H | H | $i\text{-}C_3H_7$ | F | F | $-CH_2C\equiv CH$ | F | F |
| 22 | F | $C_2H_5O$ | H | $i\text{-}C_3H_7$ | F | F | $-CH_2C\equiv CH$ | F | F |
| 23 | H | $C_2H_5$ | H | $i\text{-}C_3H_7$ | F | F | $-CH_2C\equiv CH$ | F | F |
| 24 | Cl | $C_2H_5$ | H | $i\text{-}C_3H_7$ | F | F | $-CH_2C\equiv CH$ | F | F |
| 25 | F | Br | F | $i\text{-}C_3H_7$ | F | F | $-CH_2C\equiv CH$ | F | F |
| 26 | Cl | $CF_3O$ | H | $i\text{-}C_3H_7$ | F | F | $-SCH_3$ | F | F |
| 27 | Cl | $CF_3O$ | H | $i\text{-}C_3H_7$ | F | F | $-CH_2-$⌬ | F | F |
| 28 | Cl | $CF_3O$ | H | $i\text{-}C_3H_7$ | F | F | $-CH_2OCH_3$ | F | F |
| 29 | Cl | $CF_3O$ | H | $i\text{-}C_3H_7$ | F | F | $CH_3$ | F | F |
| 30 | Cl | $CF_3O$ | H | $i\text{-}C_3H_7$ | F | F | $-CH_2SCH_3$ | F | F |
| 31 | Cl | $CF_3O$ | H | $t\text{-}C_4H_9$ | F | F | $-CH_2C\equiv CH$ | F | F |

TABLE II-continued

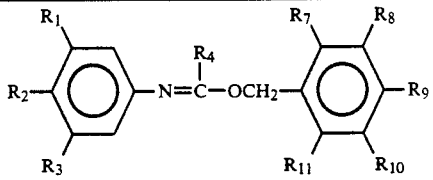

| Compound Number | R1 | R2 | R3 | R4 | R7 | R8 | R9 | R10 | R11 |
|---|---|---|---|---|---|---|---|---|---|
| 32 | Cl | CF3O | H |  | F | F | —CH2C≡CH | F | F |
| 33 | Cl | CF3O | H | CHCl2 | F | F | —CH2C≡CH | F | F |
| 34 | Cl | CF3O | H | C2H5 | F | F | —CH2C≡CH | F | F |
| 35 | Cl | CF3O | H | i-C3H7 | H | F | —CH2C≡CH | F | H |
| 36 | Cl | CF3O | H | i-C3H7 | H | F | —CH2C=CH2 | F | H |
| 37 | Cl | CF3O | H | i-C3H7 | F | H | —CH2C=CH2 | H | F |
| 38 | Cl | CHF2O | H | i-C3H7 | F | F | —CH2C≡CH | F | F |
| 39 | F | CH3 | H | i-C3H7 | F | F | —CH2C≡CH | F | F |
| 40 | Cl | Cl | H | i-C3H7 | F | F | —CH2C≡CH | F | F |
| 41 | C2H5O | H | H | i-C3H7 | F | F | —CH2C≡CH | F | F |
| 42 | Cl | CF3 | H | i-C3H7 | F | F | —CH2C≡CH | F | F |
| 43 | H | Cl | H | i-C3H7 | F | F | —CH2C≡CH | F | F |
| 44 | F | Cl | F | i-C3H7 | F | F | —CH2C≡CH | F | F |
| 45 | Cl | CF3O | H | i-C3H7 | F | F | —CH2OH | F | F |
| 46 | Cl | CF3O | H | i-C3H7 | F | F | NHCH2C≡CH | F | F |
| 47 | Cl | CF3O | H | i-C3H7 | F | F | —CH2CN | F | F |
| 48 | Cl | CF2BrO | H | i-C3H7 | F | F | —CH2C≡CH | F | F |
| 49 | Cl | Br | H | i-C3H7 | F | F | —CH2C≡CH | F | F |
| 50 | Cl | CF2ClO | H | i-C3H7 | F | F | —CH2C≡CH | F | F |
| 51 | Cl | C2H5O | H | i-C3H7 | F | F | —CH2C≡CH | F | F |
| 52 | F | C2H5O | F | i-C3H7 | F | F | —CH2C≡CH | F | F |
| 53 | Cl | CF3O | H | C(CH3)=CH2 | F | F | —CH2C≡CH | F | F |

Insecticidal Evaluation

Compounds described in Table I and II were tested for insecticidal activity using the following testing procedures. LC-50 values, based on the results of these tests and calculated according to dosage-mortality curves, are expressed in Table III.

Housefly [*Musca domestica*]

Test compounds were diluted in acetone and aliquots pipetted onto the bottom of aluminum dishes. To ensure even spreading of the chemical on the bottom of the dishes, 1 ml of acetone containing 0.01% peanut oil was also added to each dish. After all solvents had evaporated, the dishes were placed in circular cardboard cages containing 25 female houseflies, 1-2 days old. The cages were covered on the bottom with cellophane and on the top with tulle netting, and each contained a sugar-water saturated cotton plug for maintenance of the flies. Mortality was recorded after 48 hours. Test levels ranged from 100 μg/25 female houseflies downward. The LC-50 values are expressed below in Table III under the heading " HF", in terms of μg of the test compound per 25 female flies.

Black Bean Aphid [*Aphis fabae* (Scop.)]

Nasturtium plants (Tropaeolum sp.), approximately 5 cm tall, were transplanted into sandy loam soil in small cups and infested with 25-50 black bean aphids of mixed ages. Twenty-four hours later they were sprayed to the point of runoff with 50-50 acetone-water solutions of the test compounds. Treated plants were held in the greenhouse and mortality was recorded after 48 hours. Test concentrations ranged from 0.05% downward. The LC-50 values are expressed below in the table under the heading " BA" in terms of percent of the test compound in the sprayed solution.

Tobacco Budworm [*Heliothis virescens* (Fabricius)]

(a) Contact

Test compounds were diluted in a 50-50 acetone-water solution. Cotton (Gossypium sp.) cotyledons were immersed in the test solutions for 2-3 seconds and placed on a wire screen to dry. The dried leaves were placed in petri dishes containing a moistened piece of filter paper and infested with 5 second-instar tobacco budworm larvae. The dishes were placed in a high humidity chamber for 5 days, and percent mortality of the larvae recorded. Test concentrations ranged from 0.05% downward. The LD-50 values are expressed below in Table III under the heading " TBW-C" in terms of percent of the test compound in the solution.

(b) Eggs

Paper towel patches of 2-day old eggs of the tobacco budworm were dipped in acetone solutions of the test compound and placed in petri dishes containing a portion of larval rearing medium. Treated eggs were maintained at 78° F. and mortality was recorded after all control eggs had hatched and the young larvae were feeding on the media. Test concentrations ranged from 0.05% downward. The LC-50 values are expressed below in the table under the heading " TBW-E" in terms of percent of the test compound in the solution.

Cabbage Looper [*Trichoplusia ni* Hubner)]

Test compounds were diluted in a 50-50 acetone-water solution. Cotyledons of hyzini squash (*Calabacita abobrinha*), approximately 1×1.5 inches, were immersed in the test solutions for 2-3 seconds and placed on a wire screen to dry. The dried leaves were placed in petri dishes containing a moistened piece of filter paper and infested with 5 second-instar cabbage looper larvae. The dishes were placed in a high humidity chamber. Mortality of the larvae was recorded 3-5 days later. Test concentrations ranged from 0.005% downward. The LC-50 value is expressed below in the table under the heading " CL" in terms of percent of the test compound in solution.

Maize Weevil [*Sitophilus zeamais* (Motschulsky)]

Test compounds were diluted in a 50-50 acetone-water solution. Four corn seeds [Zea mays (L.)] which had been immersed in test solutions for 2-3 seconds and allowed to dry were placed in containers together with 10 adult weevils. The containers were covered and kept at a temperature of about 25° C. Mortality was recorded after 48 hours. Test concentrations ranged from 0.1% down to that at which 50% mortality occurred. The LC-50 value is expressed below in the table under the heading " MW" in terms of percent of the test compound in solution.

Aster Leafhopper [*Macrosteles fascifrens* (Stal)]

Oat seedlings (Avena sp.) were grown in a commercial potting soil in cups. When the plants were approximately 10 cm tall, they were thinned to three plants per cup and dipped for 2-3 seconds in 50-50 acetone-water solutions of the test compounds. When the plants had dried, a clear plastic tube was placed over them and the bottom end pressed into the cup. Ten aster leafhopper adults/nymphs were then placed in each tube and the tops of the tubes covered with white organdy cloth. Mortality counts were made after 48 hours. Test concentrations ranged from 0.001% down to that at which 50% mortality occurred. The LC-50 values are expressed below in Table III under the heading " LH" in terms of the percent of the test compound in the solution.

Rice water weevil [*Lissorhoptrus oryzophilus* (Kuschel)]

Test compounds were diluted in acetone. Droplets (1 ul) of test solutions were applied to the ventral abdomens of ten female adult weevils. The treated weevils were placed in containers with wet cotton balls and rice foliage. The containers were covered and kept at a temperature of about 25° C. Mortality was recorded after 48 hours. Test concentrations ranged from 0.3 mg/ml or 0.3 µg per weevil down to that at which 50% mortality occurred. The LC-50 values are expressed below in Table III under the heading " RWW" in terms of µg of test compound per weevil.

Acaricidal Evaluation Test

The two-spotted mite (2SM) [*Tetranychus urticae* (Koch)] was employed in tests for miticides. The test procedure was as follows:

Pinto bean plants (Phaseolus sp.), approximately 10 cm tall, were transplanted into sandy loam soil in small cups and thoroughly infested with two-spotted mites of mixed ages and sexes. Twenty-four hours later the infested plants were inverted and dipped for 2-3 seconds in 50-50 acetone-water solutions of the test compounds. Treated plants were held in the greenhouse, and 5-7 days later mortality was determined for both adult mites and the nymphs hatching from eggs which were on the plants at the time of treatment. Test concentrations ranged from 0.05% downward. The LC-50 values are expressed below in Table III under the headings " 2SM-A" (i.e., adults) and " 2SM-E" (i.e. eggs) in terms of percent concentration of the test compound in the solution.

TABLE III

| Compound Number | HF, µg* | BA, % | 2-SM A, % | 2-SM E, % | TBW C, % | TBW E, % | CL, % | MZW, % | LH, % | RWW, µg |
|---|---|---|---|---|---|---|---|---|---|---|
| 1 | — | 0.0003 | >0.005 | >0.005 | — | >0.05 | 0.0038 | >0.01 | — | — |
| 2 | — | 0.001 | >0.005 | >0.005 | — | >0.05 | 0.0004 | >0.01 | — | — |
| 3 | — | 0.005 | >0.005 | >0.005 | — | >0.05 | >0.005 | >0.01 | — | — |
| 4 | — | 0.003 | >0.005 | >0.005 | — | — | >0.0025 | >0.01 | — | — |
| 5 | — | >0.005 | >0.005 | >0.005 | — | — | 0.0019 | >0.005 | — | — |
| 6 | — | 0.0001 | >0.0025 | >0.001 | >0.005 | 0.038 | 0.00038 | — | — | 0.07 |
| 7 | 20 | — | >0.05 | >0.05 | — | >0.1 | 0.00045 | — | — | — |
| 8 | 21 | 0.006 | >0.05 | >0.05 | — | 0.08 | 0.001 | >0.01 | — | — |
| 9 | 6 | — | >0.05 | >0.05 | — | 0.04 | 0.003 | — | — | — |
| 10 | 14 | 0.002 | >0.05 | >0.05 | — | 0.09 | 0.0024 | >0.01 | — | — |
| 11 | 6 | 0.0002 | >0.05 | >0.05 | 0.00075 | 0.017 | 0.00005 | 0.0042 | 0.00025 | — |
| 12 | >100 | 0.005 | 0.01 | 0.01 | — | — | >0.001 | >0.01 | >0.001 | — |
| 13 | >10 | 0.001 | >0.05 | >0.05 | — | >0.025 | 0.0001 | 0.0032 | — | >0.075 |
| 14 | >100 | 0.0006 | >0.05 | >0.05 | — | 0.05 | 0.0005 | >0.0075 | 0.001 | — |
| 15 | 10 | 0.00008 | 0.003 | 0.008 | 0.0009 | 0.01 | 0.000075 | 0.0035 | 0.00002 | 0.062 |
| 16 | >10 | 0.0001 | 0.003 | >0.01 | 0.0045 | 0.025 | 0.0002 | 0.0017 | — | — |
| 17 | — | 0.002 | >0.005 | >0.005 | — | 0.039 | 0.0016 | >0.01 | 0.0001 | — |
| 18 | — | 0.0001 | >0.005 | >0.005 | — | 0.017 | 0.0002 | >0.01 | 0.00008 | — |
| 19 | — | 0.0003 | 0.005 | 0.005 | — | 0.018 | 0.00038 | 0.0075 | — | — |
| 20 | — | 0.0001 | >0.005 | >0.005 | — | 0.0085 | 0.00012 | >0.01 | 0.0002 | — |
| 21 | — | 0.0006 | >0.005 | >0.005 | — | 0.017 | 0.00016 | 0.004 | — | — |
| 22 | — | 0.0002 | >0.005 | >0.005 | — | >0.05 | 0.0025 | 0.0075 | — | — |
| 23 | — | >0.00025 | — | — | — | — | 0.0005 | >0.1 | — | — |
| 24 | — | 0.0002 | >0.005 | >0.005 | — | 0.027 | 0.00035 | >0.01 | — | — |
| 25 | — | 0.0003 | >0.005 | >0.005 | — | 0.017 | 0.0002 | 0.008 | — | — |
| 26 | — | 0.005 | >0.005 | >0.005 | — | >0.05 | 0.003 | >0.1 | — | — |
| 27 | — | 0.001 | >0.005 | >0.005 | — | >0.05 | >0.005 | >0.1 | — | >0.08 |
| 28 | — | 0.001 | >0.005 | >0.005 | — | 0.05 | 0.00006 | 0.007 | — | — |
| 29 | — | 0.005 | >0.005 | >0.005 | — | 0.038 | 0.00018 | 0.005 | — | — |
| 30 | — | 0.0003 | >0.005 | >0.005 | — | 0.038 | 0.0004 | >0.01 | — | — |
| 31 | — | 0.0005 | — | — | — | — | 0.0004 | — | — | — |
| 32 | — | 0.0001 | 0.003 | 0.005 | — | 0.017 | 0.00003 | >0.01 | 0.00003 | — |
| 33 | — | >0.00025 | — | — | — | — | 0.00025 | — | — | — |

TABLE III-continued

| Compound Number | HF, μg* | BA, % | 2-SM A, % | 2-SM E, % | (LC$_{50}$) TBW C, % | (LC$_{50}$) TBW E, % | CL, % | MZW, % | LH, % | RWW, μg |
|---|---|---|---|---|---|---|---|---|---|---|
| 34 | — | 0.0001 | 0.005 | 0.005 | — | 0.018 | 0.00007 | >0.01 | — | — |
| 35 | — | 0.0003 | >0.005 | >0.005 | — | 0.01 | >0.0001 | >0.01 | — | 0.07 |
| 36 | — | 0.001 | >0.005 | >0.005 | — | 0.04 | 0.00014 | >0.01 | — | — |
| 37 | — | 0.005 | >0.005 | >0.005 | — | 0.04 | 0.002 | >0.01 | — | >0.08 |
| 38 | — | 0.00025 | >0.005 | >0.005 | — | — | 0.00075 | >0.01 | — | — |
| 39 | — | 0.0002 | >0.005 | >0.005 | — | — | 0.0009 | >0.01 | — | — |
| 40 | — | 0.0001 | >0.005 | >0.005 | — | — | 0.0006 | 0.008 | — | — |
| 42 | — | 0.0003 | >0.005 | >0.005 | — | — | 0.00005 | >0.01 | — | — |
| 43 | — | 0.0003 | >0.005 | >0.005 | — | — | >0.0025 | 0.01 | — | — |
| 44 | — | 0.0003 | >0.005 | >0.005 | — | — | 0.0004 | 0.0025 | — | — |
| 45 | — | 0.005 | >0.005 | >0.005 | — | — | >0.0025 | >0.01 | — | — |
| 46 | — | 0.001 | >0.005 | >0.005 | — | — | 0.0018 | >0.01 | — | — |
| 47 | — | 0.003 | >0.005 | >0.005 | — | — | 0.0005 | >0.01 | — | — |
| 48 | — | 0.00008 | 0.0025 | 0.003 | — | — | 0.0002 | 0.0078 | — | — |
| 49 | — | 0.0003 | >0.005 | >0.005 | — | — | 0.00075 | 0.0075 | — | — |
| 50 | — | 0.0003 | >0.005 | >0.005 | — | — | 0.00022 | 0.0083 | — | — |

*per 25 female flies

The insecticidal activity, and therefore the inclusion of a compound not mentioned specifically herein within the class of compounds of this invention, as determined by the general formula, may be determined by evaluating such a compound using one or more of the above-described procedures. If a test compound demonstrates activity against one or more of the insects mentioned, by virtue of causing 50 percent or greater mortality at the initial evaluation level, it is considered "insecticidal" for the purposes of this invention.

In practice a pure compound (active compound) can be used as an insecticide. However, in general, the compounds are first formulated with one or more inert (i.e. non-chemically reactive, plant compatible or herbicidally inert) carriers or diluents suitable for insecticidal use, before being applied.

The compositions or formulations, including a compound as described herein, may take any one of a number of solid or liquid forms. Examples of solid forms are dusts, granules, tablets, powders and the like. Examples of liquid forms are emulsions, solutions, suspensions, flowables, emulsifiable concentrates and pastes. Such compositions may contain, in addition to the active compound or compounds, various carriers or diluents; surface-active agents (wetting agents, dispersing agents and/or emulsifying agents); solvents (water, or organic solvents such as aromatic solvents or chlorinated aliphatic solvents); adhesives; thickeners; binders; antifoaming agents; and other substances as mentioned herein. Solid carriers or diluents included in such compositions or formulations may include, for example, ground natural minerals such as kaolins, alumina, calcined diatomaceous earth, calcium carbonate, silica, kieselguhr, clays, etc.; ground synthetic minerals such as various silicates and alumino-silicates and ground vegetable products such as bark, cornmeal, sawdust, cellulose powder and the like. Compositions containing sorptive clays will usually also contain a stabilizer, such as a glycol, to prevent or minimize degradation of the active ingredient.

To manufacture solid compositions, the active compounds are mixed with solid carriers or diluents such as those mentioned above and the mixture is ground to the appropriate size. Granules can be manufactured by dissolving an active compound in an organic solvent and applying the mixture, for example, by atomization, onto an absorptive granulated inert material, such as silica. Adhesives may be utilized to assist in the incorporation of the compound onto the solid particles.

Wettable powders and pastes are obtained by mixing and grinding an active compound with one or more dispersing agents and/or solid carriers or diluents. Also included may be wetting agents and/or dispersing agents, for example, lignins, methyl cellulose, naphthalenesulfonic acid derivatives, fatty alcohol sulfates and various types of alkali and alkaline earth metal salts of fatty acids.

Emulsifiable concentrates are generally obtained by dissolving the active compound in an organic solvent, for example, butanol, cyclo-hexanone, xylenes, or higher boiling aromatic hydrocarbons. To obtain suspensions or emulsions in water, wetting agents may also be added.

Flowables are prepared by mixing an active compound with one or more dispersing agents and/or solid additives, and a liquid (which may be water or an organic solvent) in which the active compound is relatively insoluble, and grinding the mixture.

Both liquid and solid compositions may be in microcapsule or encapsulated form, to permit release of the enclosed active compound at a controlled rate over a period of time. Liquid compositions of this type contain encapsulated droplets of approximately 1–50 microns in diameter, including the active compound and optionally a solvent. The encapsulating material is an inert porous membrane of a polymeric material.

Solid encapsulated compositions generally take the form of granules, in which the liquid containing the active component is trapped in the pores of the granular support by a porous polymeric membrane through which the active ingredient may migrate at a controlled rate, or which membrane breaks down at a controlled rate to permit escape of the active ingredient.

Typical encapsulating materials include natural and synthetic rubbers, cellulosic materials, styrene-butadiene copolymers, polyacrylonitriles, polyacrylates, polyamides, polyisocyanates, polyurethanes, mixed copolymers of the foregoing and starch xanthates.

It is possible to use highly concentrated liquid compositions containing up to about 95% by weight of the active compound, or even the 100% active compound alone, when applying the compound in the form of a finely divided liquid by use of various atomizing equipment, for example by airplane spraying techniques. For other purposes, however, the various types of compositions which can be utilized for these compounds will contain varying amounts of the compound according to the type of composition and the intended use.

In general, insecticidal compositions may contain from 5 to 95% of the active compound, more preferably from 10 to 85%. Some typical compositions will contain an active compound as follows: wettable powders: 25 to 80% active compound; oil suspensions, emulsions, solutions, flowables, and emulsifiable concentrates: 5 to 85% active compound; aqueous suspensions: 20 to 50% active compound; dusts and powders: 5 to 20% active compound; granules and pellets: 5 to 20% active compound.

In addition to the active compound and the various agents utilized in preparing compositions and formulations mentioned, such compositions may also contain one or more other active compounds of the type mentioned herein, as well as other active pesticidal agents such as herbicides, fungicides, insecticides, acaricides, nematocides, bactericides, and plant growth regulators. The particular pesticide included in the mixture will depend upon its intended utility and the type of complementary action required. Examples of suitable insecticides include the following:

(a) natural pyrethrins or pyrethroids such as permethrin, esfenvalerate, deltamethrin, cyhalothrin, biphenthrin, fenpropathrin, cyfluthrin, tefluthrin, empenthrin, ethofenprox, tetramethrin, bioallethrin, fenfluthrin, prallethrin, 5-benzyl-3-furylmethyl-(E)-(IR,3S)-2,2-dimethyl-3-(2-oxothiolan-3-ylidene-methyl)cyclopropane carboxylate, and pentafluorobenzyl (cis)-3-[2-fluoro-2(methoxycarbonyl)ethenyl]-2,2-dimethylcyclopropane carboxylate;

(b) organophosphates such as profenofos, sulprofos, phosmet, dichlorvos, methyl parathion, azinphos-methyl, dimeton-s-methyl, heptenophos, thiometon, fenamiphos, monocrotophos, triazophos, methamidophos, dimethoate, phosphamidon, malathion, chlorpyrifos, phosalone, fensulfothion, fonofos, phorate, phoxim, pyrimiphosmethyl, fenitrothion and diazinon;

(c) carbamates (including aryl carbamates) such as pirimicarb, cloethocarb, carbofuran, ethiofencarb, aldicarb, thiofurox, carbosulfan, bendiocarb, fenobucarb, propoxur and oxamyl;

(d) benzoyl ureas such as triflumuron and chlorofluazuron;

(e) organic tin compounds such as cyhexatin, fenbutatin oxide, and azocyclotin;

(f) macrolides such as avermectins or milbemycins, such as abamectin, avermectin, and milbemycin;

(g) hormones and synthetic mimics thereof such as juvenile hormone, juvabione, ecdysones, methoprene and hydroprene;

(h) pheromones; and (i) organochlorine compounds such as benzene hexachloride, DDT, chlordane or dieldrin.

In addition to the major chemical classes of insecticides listed above, other insecticides having particular targets may be employed in the mixture if appropriate for the intended utility of the mixture. For instance, selective insecticides for particular crops, for example stemborer-specific insecticides for use in rice such as cartap or buprofesin, can be employed. Alternatively, insecticides specific for particular insect species/stages, for example ovolarvicides such as clofentezine, amitraz, chlordimeform, flubenzimine, hexythiazox and tetradifon, motilicides such as dicofol or propargite, adulticides such as bromopropylate, chlorobenzilate, or insect growth regulators such as hydramethylon, cyromazine, methoprene, chlorofluazuron and diflubenzuron may also be included in the compositions. Such compositions may also contain soil disinfectants or fumigants and may further contain fertilizers, thus making it possible to provide multi-purpose compositions containing one or more of the active compounds described herein as well as, optionally, other pesticides and also fertilizers, all intended and formulated for use at the same locus.

Control of insect pests is accomplished by applying a composition containing an insecticidally effective amount of an active compound as described herein to the insect, to a locus at which insecticidal control is desired, or to food sources (including seeds) on which the insects feed. For use in the last mentioned manner, it is preferable to utilize a compound which is not volatile. Thus, control may be achieved by direct application of the active compounds to the insects and indirectly by application of the compounds to a locus to be protected (such as crop lands, grass ranges and forests), to a source of food for insects or to other insect habitats (for example, breeding or swarming areas). The rates of application of the active compound and the concentration applied will vary according to whether the compound or composition is being directly applied to the insect or indirectly, to a locus, food or habitat. In the latter case, the rate of the application, depending on the nature of the insect or insects to be controlled, and the plant environment, will generally vary from about 0.01 to about 100 pounds per acre (about 0.011 to about 111 kg/ha).

It should be noted that the active compound need not be insecticidally active per se to effect insect control. The purposes of this invention are fully served if such compounds are rendered active by external influences, such as light or heat, or by some physiological action which occurs when the compound is ingested into the body of the insect.

Compounds of this invention could be used to control a variety of insects such as:
*Myzus persicae* (aphid)
*Aphis gossypii* (aphid)
*Aphis fabae* (aphid)
*Megoura viceae* (aphid)
*Aedes aegypti* (mosquito)
Anopheles spp. (mosquitos)
Culex spp. (mosquitos)
*Dysdercus fasciatus* (capsid)
*Musca domestica* (housefly)
*Pieris brassicae* (white butterfly)
*Plutella maculipennis* (diamond back moth)
*Phaedon cochlaeriae* (mustard beetle)
Aonidiella spp. (scale insects)
Trialeuroides spp. (white flies)
*Bemisia tabaci* (white fly)
*Blattella germanica* (cockroach)
*Periplaneta americana* (cockroach)
*Blatta orientalis* (cockroach)
*Spodoptera littoralis* (cotton leafworm)
*Heliothis virescens* (tobacco budworm)
*Chortiocetes terminifera* (locust)
Diabrotica spp. (rootworms)
Agrotis spp. (cutworms)
*Chilo supressalis* (stem borer)
*Chilo partellus* (maize stem borer)
*Nilaparvata lugens* (planthopper)
*Nephottex virescens* (leafhopper)
*Nephotettix cincticeps* (leafhopper)

*Panonychus ulmi* (European red mite)
*Panonychus citri* (citrus red mite)
*Tetranychus urticae* (two-spotted spider mite)
*Tetranychus cinnabarinus* (carmine spider mite)
*Phyllcoptruta oleivora* (citrus rust mite)
*Polyphagotarsonemus latus* (broad mite)
Brevipalpus spp. (mites)

Compositions containing one or more of the active compounds described, in an insecticidally effective amount, may be applied to the plant, locus, insect or insect habitat in any conventional manner.

When used in connection with crop or other plant protection, application may be made in a preventive (i.e. before infestation) or eradicative manner (i.e., after infestation). Thus, powders and various liquid compositions containing the active compound can be applied by the use of power dusters, boom and hand sprayers and spray dusters, or applied from airplanes as dusts or sprays. When applied in the latter method, they may be effective in very low dosages.

Compositions including active compounds may also be applied by addition to irrigation waters supplied to the field to be treated. This method of application permits penetration of the compounds into the soil as the water is absorbed therein.

Compositions including active compounds may additionally be used to protect plant seeds from being attacked by soil-borne insect pests after planting and during germination, by applying the composition to the seeds as a seed dressing. This is performed generally by mixing the seeds with an active composition in either liquid or solid form (preferably liquid) in a suitable mixing apparatus. Liquid compositions for this purpose may contain an adhesive or sticking agent, such as methyl cellulose, ethyl cellulose, etc., to assist the composition in adhering to the seed. If a solid composition is utilized for this purpose, an adhesive agent may be sprayed on the seeds during or after mixing.

For use as a soil insecticide, the active compound, or compositions containing it, may be mixed with the soil in any conventional manner, before, during or after planting of the plant seeds. Liquid compositions may be applied by spraying onto the surface or by incorporation in irrigation or sprayed water. Solid or liquid compositions containing an active compound may be incorporated into the soil prior to or during planting by discing, plowing or other mixing operations, in order to locate the active ingredient below the surface of the soil so as to be most effective in controlling undesirable larvae.

Some examples of compositions containing the active compounds of this invention are:

| Component | Weight % |
|---|---|
| Composition A: Granular Solid | |
| Active compound | 10 |
| attapulgite clay granules | 85 |
| triethylene glycol | 5 |
| Total | 100% |
| Composition B: Wettable Powder | |
| Active compound | 80 |
| wetting agent (sodium dialkyl-naphthalene sulfonate) | 1 |
| dispersing agent (sodium lignosulfonate) | 4 |
| diluent (aluminum magnesium silicate) | 15 |
| Total | 100% |

| Component | Weight % |
|---|---|
| Composition C: Dilute Solution | |
| Active compound | 5 |
| solvent (xylene) | 95 |
| Total | 100% |
| Composition D: Emulsifiable Concentrate | |
| Active compound | 50 |
| Emulsifier (blend of metal sulfonates and polyoxyethylene ethers) | 10 |
| solvent (xylene) | 40 |
| Total | 100% |
| Composition E: Concentrated Solution | |
| Active compound | 90 |
| solvent (xylene) | 10 |
| Total | 100% |

What is claimed is:

1. A compound having the formula

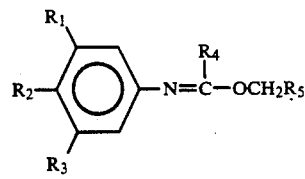

in which
$R_1$ is hydrogen, halogen, $C_1$-$C_4$ alkoxy, $C_1$-$C_4$ haloalkyl, $C_1$-$C_4$ haloalkoxy or $C_1$-$C_4$ haloalkylthio;
$R_2$ is hydrogen, halogen, $C_1$-$C_4$ alkyl, $C_1$-$C_4$ alkoxy, $C_1$-$C_4$ haloalkyl, $C_1$-$C_4$ haloalkoxy or $C_1$-$C_4$ haloalkylthio;
$R_3$ is hydrogen, halogen or $C_1$-$C_4$ haloalkyl; or
$R_1$ and $R_2$ taken together are $C_1$-$C_4$ alkyleneoxy or halo-$C_1$-$C_3$ alkyleneoxy;
provided that $R_1$, $R_2$ and $R_3$ are not all hydrogen;
$R_4$ is methyl, ethyl, n-propyl, $C_3$-$C_7$ branched alkyl, $C_1$-$C_6$ haloalkyl, $C_2$-$C_6$ alkenyl; or cyclopropyl, optionally substituted by up to 4 methyl groups or up to 2 halogens;
$R_5$ is:

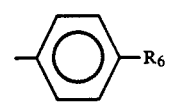

(a)

or

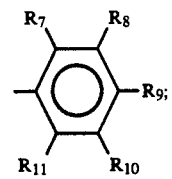

(b)

$R_6$ is benzyl, $C_3$-$C_4$ alkenyl, or $C_3$ alkynyl;
$R_7$, $R_8$, $R_{10}$ and $R_{11}$ are each fluoro; and
$R_9$ is methoxymethyl, $C_3$-$C_4$ alkenyl or $C_3$ alkynyl.

2. A compound according to claim 1 in which $R_3$ is hydrogen.

3. A compound according to claim 1 in which $R_4$ is ethyl, isopropyl, isopropenyl, dichloromethyl or cyclopropyl.

4. A compound according to claim 1 in which $R_1$ is hydrogen, halogen, trifluoromethyl, difluoromethoxy, difluorobromomethoxy or difluorochloromethoxy; $R_2$ is hydrogen, halogen, $C_1$-$C_4$ alkyl, $C_1$-$C_4$ alkoxy, $C_1$-$C_4$ haloalkoxy or trifluoromethyl; and $R_3$ is hydrogen.

5. A compound according to claim 4 in which $R_1$ is halogen and $R_2$ is trifluoromethoxy.

6. A compound according to claim 1 in which $R_5$ is

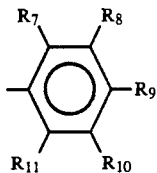

and $R_7$, $R_8$, $R_{10}$ and $R_{11}$ are each fluoro.

7. A compound according to claim 6 in which $R_9$ is methoxymethyl, allyl, 2-methylalkyl or 2-propynyl.

8. A compound according to claim 6 in which $R_1$ is chloro, $R_2$ is trifluoromethoxy, $R_3$ is hydrogen, $R_4$ is isopropyl and $R_9$ is 2-propynyl.

9. A compound according to claim 6 in which $R_1$ and $R_2$ taken together are difluoromethylenedioxy, $R_3$ is hydrogen, $R_4$ is isopropyl and $R_9$ is 2-propynyl.

10. A compound according to claim 6 in which $R_1$ is chloro, $R_2$ is trifluoromethoxy, $R_3$ is hydrogen, $R_4$ is isopropyl and $R_9$ is methoxymethyl.

11. A compound according to claim 6 in which $R_1$ is chloro, $R_2$ is trifluoromethoxy, $R_3$ is hydrogen, $R_4$ is cyclopropyl and $R_9$ is 2-propynyl.

12. A compound according to claim 6 in which $R_1$ is chloro, $R_2$ is trifluoromethoxy, $R_3$ is hydrogen, $R_4$ is ethyl and $R_9$ is 2-propynyl.

13. A compound according to claim 6 in which $R_1$ is chloro, $R_2$ is trifluoromethoxy, $R_3$ is hydrogen, $R_4$ is isopropyl and $R_9$ is 2-propynyl.

14. A method for controlling insects comprising applying to an insect, the locus of an insect, or a locus at which insecticidal control is desired, an insecticidally effective amount of a compound according to claim 1.

15. An insecticidal composition comprising: (a) an insecticidally effective amount of a compound according to claim 1; and (b) an insecticidally suitable diluent or carrier.

* * * * *